United States Patent [19]

Tanaka et al.

[11] 4,094,872
[45] June 13, 1978

[54] 7-(β-AMINOACYLAMINO)-3-HETEROCYCLIC-THIOMETHYL-3-CEPHEM-4-CARBOXYLIC ACID DERIVATIVES

[75] Inventors: Kunihiko Tanaka, Hattori; Masaru Kurita, Takatsuki; Osamu Nishiwaki, Sakai, all of Japan

[73] Assignee: Fujisawa Pharmaceutical Co., Ltd., Osaka, Japan

[21] Appl. No.: 396,580

[22] Filed: Sep. 12, 1973

[30] Foreign Application Priority Data

Nov. 17, 1972 Japan ................. 47-115983

[51] Int. Cl.² ............... C07D 501/54; C07D 501/56; A61K 31/545
[52] U.S. Cl. ..................... 544/26; 424/246; 544/27; 544/28; 544/29; 544/30
[58] Field of Search ................... 260/243 C

[56] References Cited

U.S. PATENT DOCUMENTS

| | | | |
|---|---|---|---|
| 3,741,963 | 6/1973 | Dursch et al. | 260/243 C |
| 3,759,904 | 9/1973 | Crast | 260/243 C |
| 3,819,620 | 6/1974 | Dursch et al. | 260/243 C |
| 3,855,213 | 12/1974 | Dunn et al. | 260/243 C |
| 3,864,340 | 2/1975 | Ishimaru et al. | 260/243 C |
| 3,867,380 | 2/1975 | Dunn et al. | 260/243 C |
| 3,898,217 | 8/1975 | Sellstedt et al. | 260/243 C |
| 3,923,795 | 12/1975 | Spry | 260/243 C |

FOREIGN PATENT DOCUMENTS

67/7,474 3/1967 Japan.

*Primary Examiner*—Nicholas S. Rizzo
*Assistant Examiner*—Diana G. Rivers
*Attorney, Agent, or Firm*—Dayton R. Stemple, Jr.

[57] ABSTRACT

7-[β-Aminoacylamino]-3-substituted-3-cephem-4-carboxylic acid derivatives of the formula:

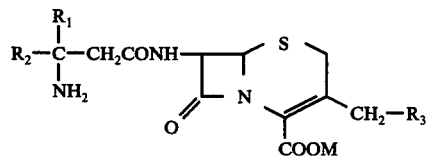

wherein
  $R_1$ is hydrogen, lower alkyl, lower alkenyl, aryl or a heterocyclic group,
  $R_2$ is hydrogen or lower alkyl, or
  $R_1$ and $R_2$ mean, taken together with the adjacent carbon atom, cycloalkyl or cycloalkenyl,
  $R_3$ is hydrogen, lower alkylthio or a hetero cyclicthio group, and
  M is hydrogen or a nontoxic, pharmaceutically acceptable cation, processes for the preparation of the same and composition thereof. These compounds are useful as antibacterial agents.

8 Claims, No Drawings

7-(β-AMINOACYLAMINO)-3-HETEROCYCLIC-THIOMETHYL-3-CEPHEM-4-CARBOXYLIC ACID DERIVATIVES

This invention relates to new cephalosporanic acid derivatives which possess an antibacterial activity, processes for preparing the same and a composition thereof.

The cephalosporanic acid derivatives can be represented by the following general formula I:

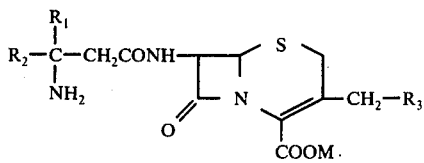

wherein $R_1$ is hydrogen, lower alkyl, lower alkenyl, aryl or a heterocyclic group, $R_2$ is hydrogen or lower alkyl, or $R_1$ and $R_2$ mean, taken together with the adjacent carbon atom, cycloalkyl or cycloalkenyl, $R_3$ is hydrogen, lower alkylthio or a hetero cyclic-thio group, and M is hydrogen or a nontoxic, pharmaceutically acceptable cation.

The term "lower alkyl" represented by $R_1$ and $R_2$ means a monovalent, straight or branched chain or cyclic, aliphatic hydrocarbon radical having one to six carbon atoms. Examples of such lower alkyl radical are methyl, ethyl, propyl, isopropyl, butyl, isobutyl, t-butyl, pentyl, hexyl, cyclopentyl, cyclohexyl, and the like.

The term "lower alkenyl" represented by $R_1$ means a monovalent, straight or branched chain or cyclic, aliphatic hydrocarbon radical containing a double bond and having two to six carbon atoms. Examples of such lower alkenyl radical are vinyl, allyl, 1-propenyl, 1-butenyl, 2-butenyl, 3-butenyl, 1-isobutenyl, 3-pentenyl, 1-cyclohexenyl, and the like.

The term "aryl" represented by $R_1$ means a monovalent aromatic hydrocarbon radical which may be substituted by halogen, nitro or lower alkoxy. Examples of such aryl radical are phenyl, naphthyl, tolyl, chlorophenyl, bromophenyl, nitrophenyl, methoxyphenyl, ethoxyphenyl, propoxyphenyl, t-butoxyphenyl, and the like.

The term "heterocyclic group" represented by $R_1$ means a monovalent, five or six membered heterocyclic radical containing one or more hetero atoms such as nitrogen, oxygen and sulphur, which may be substituted by halogen, nitro, lower alkyl or lower alkoxy. Examples of such heterocyclic group are furyl, thienyl, pyrrolyl, imidazolyl, pyrazolyl, thiazolyl, oxazolyl, triazolyl, thiadiazolyl, oxadiazolyl, tetrazolyl, pyridyl, pyridazinyl, pyrimidinyl, pyrazinyl, chlorothienyl, nitrofuryl, methylthiadiazolyl, methyloxadiazolyl, methyltetrazolyl, methoxypyridyl, and the like.

The term "cycloalkyl" formed by the linkage of $R_1$ and $R_2$ means a monovalent cyclic aliphatic hydrocarbon radical having five to seven carbon atoms. Examples of such cycloalkyl radical are cyclopentyl, cyclohexyl and cycloheptyl.

The term "cycloalkenyl" formed by the linkage of $R_1$ and $R_2$ means a monovalent cyclic aliphatic hydrocarbon radical containing one or more double bonds and having five to seven carbon atoms. Examples of such cycloalkenyl radical are cyclopentenyl, cyclohexenyl, cycloheptenyl, cyclohexadienyl, and the like.

The term "lower alkylthio" represented by $R_3$ means a monovalent straight or branched chain hydrocarbonthio radical having one to four carbon atoms. Examples of such lower alkylthio radical are methylthio, ethylthio, propylthio, isopropylthio, butylthio, isobutylthio and t-butylthio.

The term "heterocyclic-thio group" represented by $R_3$ means a monovalent, five membered heterocyclic-thio radical containing one or more hetero atoms such as nitrogen, oxygen and sulphur, which may be substituted by alkyl. Examples of such heterocyclic-thio groups are thiazolylthio, oxazolylthio, 1,2,4-thiadiazolylthio, 1,3,4-thiadiazolylthio, 1,2,5-thiadiazolylthio, 1,2,4-oxadiazolylthio, 1,3,4-oxadiazolylthio, 1,2,5-oxadiazolylthio, 1,2,4-triazolylthio, 1,3,4-triazolylthio, 1,2,5-triazolylthio, 1-methyl-1H-tetrazolylthio, 2-methyl-2H-tetrazolylthio, 5-methyl-1,3,4-thiadiazolylthio, 3-methyl-1,2,4-thiadiazolylthio, 5-methyl-1,3,4-oxadiazolylthio, and the like.

The term "nontoxic, pharmaceutically acceptable cation" means an alkali metal such as sodium, potassium, and the like.

The objective cephalosporanic acid derivatives I may be prepared by acylating 7-amino-3-substituted-3-cephem-4-carboxylic acids of formula II:

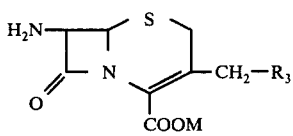

wherein $R_3$ and M are as defined above, with β-amino aliphatic carboxylic acid derivatives of formula III:

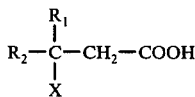

wherein $R_1$ and $R_2$ are as defined above and X is protected amino,
or their reactive derivatives and then, if necessary, removing a protective group on the amino radical.

The term "protected amino" represented by X in the formula III means an amino radical having a protective group such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, 4-(phenylazo)benzyloxycarbonyl, 4-(4-methoxyphenylazo)benzyloxycarbonyl, t-butoxycarbonyl, t-pentyloxycarbonyl, isopropoxycarbonyl, diphenylmethoxycarbonyl, 2-pyridylmethoxycarbonyl, 2,2,2-trichloroethoxycarbonyl, 2,2,2-tribromoethoxycarbonyl, 1-cyclopropylethoxycarbonyl, 3-iodopropoxycarbonyl, 2-furfuryloxycarbonyl, 1-adamantyloxycarbonyl, 8-quinolyloxycarbonyl, trifluoroacetyl, trityl, 2-nitrophenylthio, 2,4-dinitrophenylthio, 2-hydroxybenzylidene, 2-hydroxy-5-chlorobenzylidene, 2-hydroxy-1-naphthylmethylene, 3-hydroxy-4-pyridylmethylene, 1-methoxycarbonyl-2-propylidene, 1-ethoxycarbonyl-2-propylidene, 3-ethoxycarbonyl-2-butylidene, 1-acetyl-2-propylidene, 1-propionyl-2-propylidene, 1-benzoyl-2-propylidene, 1,3-bis(ethoxycarbonyl)-2-propylidene, 1-(N-methylcarbamoyl)-2-propylidene, 1-(N,N-dimethylcarbamoyl)-2-propylidene, 1-[N-(2-methoxyphenyl)carbamoyl]-2-propylidene, 1-[N-(4-methoxyphenyl)carbamoyl]-2-propylidene, 1-(N-phenylcarbamoyl)-2-propylidene, 2-ethoxycarbonylcyclopentylidene, 2-ethoxycarbonylcyclohexylidene, 2-acetylcyclohexylidene, 3,3-dimethyl-5-oxocyclohexylidene, or the like.

Furthermore, acid salts such as hydrochloride, hydrobromide, hydroiodide of the free amino radical are also exemplified as the protected amino.

The acylation reaction may be carried out in a conventional manner, for instance, in a solvent such as acetone, dioxane, acetonitrile, chloroform, ethylenechloride, tetrahydrofuran, ethyl acetate, dimethylformamide, pyridine or water, or any other appropriate organic solvents. The reaction may be preferably carried out under cooling or at room temperature.

When the β-amino aliphatic carboxylic acid derivatives of formula III are employed in the form of their free acids or their salts, the acylation reaction may be effected in the presence of a condensing agent, for example, such as N,N'-dicyclohexylcarbodiimide, thionylchloride, or the like. Suitable reactive derivatives of the β-amino aliphatic carboxylic acid derivatives III may include carboxylic acid halides, active amides, active esters, acid anhydrides or mixed anhydrides with the other carboxylic acids.

The acylation reaction also may be carried out after treating the 7-amino-3-substituted-3-cephem-4-carboxylic acids II with a silylating agent such as chlorotrimethylsilane, bis[N,N-trimethylsilyl]acetamide, N-trimethylsilylacetamide, or the like.

The acylation is followed, if necessary, by removing reaction of the protective group on the amino radical, and the silyl group.

The removing reaction of the protective group on the amino radical may be carried out in a conventional manner, for instance, by treating the acylation resultant with acids such as formic acid, trifluoroacetic acid, and the like, or by catalytic reduction, although depending upon the protective group to be removed.

The removing reaction using acids may be adopted for the compounds having such protective group as benzyloxycarbonyl, substituted benzyloxycarbonyl, alkoxycarbonyl, substituted alkoxycarbonyl, aralkoxycarbonyl, adamantyloxycarbonyl, trityl, substituted phenylthio, substituted aralkylidene, substituted alkylidene, substituted cycloalkylidene, or the like. The removing reaction by the catalytic reduction may be adopted for the compounds having such protective group as benzyloxycarbonyl, substituted benzyloxycarbonyl, 2-pyridylmethoxy carbonyl, or the like. When the protective group is trifluoroacetyl, it may be removed by treating the acylation resultant with water, and when the protective group is haloalkoxycarbonyl or 8-quinolyloxycarbonyl, they may be removed by treating the acylation resultant with copper, zinc, or the like.

The removing reaction of the silyl group, which is usually removed easily by the post-treatment of the acylation resultant in the acylation reaction, may be carried out by treating the acylation resultant with water.

It should be understood that these removing reactions of the protective group on the amino radical and the silyl group may be carried out without the isolation of the acylation resultant from the reaction medium.

Alternatively, some of the desired compounds of the present invention may be prepared by reacting the 7-acylated aminocephalosporanic acids of formula IV:

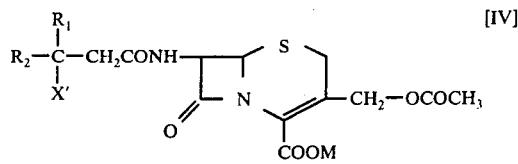

wherein $R_1$, $R_2$ and M are as defined above and X' is amino or protected amino, which may be prepared by reacting 7-aminocephalosporanic acid with the β-amino aliphatic carboxylic acid derivatives and then, if necessary, removing the protective group on the amino radical, with nucleophiles of the formula V:

$$R_3'-H \qquad [V]$$

wherein $R_3'$ is lower alkylthio or a heterocyclic-thio group, or their alkali metal salts, and the other of the desired compounds of the present invention may be prepared by reducing the 7-acylated aminocephalosporanic acids IV in a conventional manner.

The reaction of the 7-acylated aminocephalosporanic acids IV with the nucleophiles V may be carried out in a solvent such as water, acetone, chloroform, nitrobenzene, dimethylformamide, methanol, ethanol, dimethylsulfoxide, or any other appropriate organic solvents. The reaction may be carried out at room temperature or under warming. When the nucleophiles V are used in the form of their free thiols, the reaction is preferably carried out in the presence of a base such as an alkali metal hydroxide, an alkali metal carbonate, an alkali metal bicarbonate, trialkylamine, or the like. And when the 7-acylated aminocephalosporanic acids IV in which X' is protected amino are employed in the reaction, the objective compounds I' of the present invention may be obtained by removing the protective group on the amino radical in a conventional manner as stated above.

The compounds of formula I':

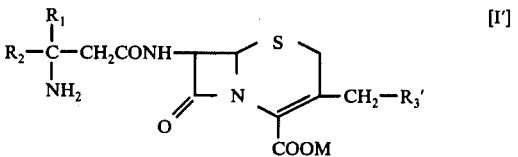

wherein $R_1$, $R_2$, $R_3'$ and M are as defined above, are prepared by the above reaction.

The reduction of the 7-acylated aminocephalosporanic acids IV may be carried out in a similar manner to the method described in U.S. Pat. No. 3,507,861, for instance, by catalytically reducing the compounds IV in a solvent such as water, ethanol, dimethylformamide, and the like, using a catalyst such as platinum, paradium, or the like, at atmospheric pressure or at high pressure. When the 7-acylated aminocephalosporanic acids IV in which X' is protected amino are employed in the reduction, the objective compounds I''' of the present invention may be obtained, if necessary, by removing the protective group on the amino radical in a conventional manner as stated above.

The compounds of formula I'':

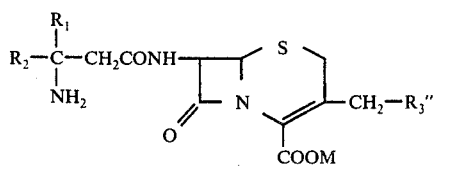

wherein $R_1$, $R_2$ and M are as defined above, and $R_3''$ is hydrogen,
are obtained by the above reaction.

As is well known to the art, the majority of the objective compounds contain one asymmetric carbon atom and can exist in two optically active isomeric forms, or in D- and L- forms. It is to be understood that the present invention includes both the D- and L- forms and the DL-mixtures.

All the reactants to be employed in the various processes of the present invention may be commercially available or be prepared by conventional methods well known to the art or by a variety of analogous methods applicable to production of such reactants.

In accordance with the present invention, a precipitate which forms during the reaction is separated from the reaction mixture by methods commonly used for this purpose, and the resulting reaction product may be subjected to routinely used purification procedures, for instance, to recrystallization from an appropriate solvent or a mixture of such solvents.

The compounds of the present invention may be converted by conventional methods of forming salts from acids into their pharmaceutically acceptable, substantially non-toxic salts, for instance, by reaction with an alkali metal hydroxide, an alkali metal bicarbonate, an alkali metal carbonate, or an organic base, sodium salt being preferred. The preferred method of preparing the salts consists in dissolving the acid in a solvent wherein the salt is insoluble and then adding a solution of the salt-forming compound or the base thereto. Thereby the salt precipitates from the reaction mixture.

The compounds of the present invention exhibit a high antibacterial activity and inhibit the growth of a number of microorganisms including Gram-positive and Gram-negative bacteria. For therapeutic administration the cephalosporin compounds according to the present invention are used in the form of pharmaceutical preparation which contain said compounds in admixture with a pharmaceutically acceptable organic or inorganic solid or liquid excipient suitable for oral or parenteral administration. The pharmaceutical preparations may be in solid form such as capsules, tablets, or dragees, or in liquid form such as solutions, suspensions, or emulsions. If desired, there may be included in the above preparations auxilliary substances, stabilizing agents, wetting or emulsifying agents, buffers and other commonly used additives.

While the dosage of the compounds will vary from and also depend upon the age and condition of the patient, an average single dose of about 100 mg., 250 mg., and 500 mg. of the compounds according to the present invention has proved to be effective in treating diseases caused by bacterial infection. In general amounts between 10 mg. and about 1000 mg. or even more may be administered.

The following examples are given for the purpose of illustrating the present invention:

EXAMPLE 1

Pivaloyl chloride (4.9 g.) was added all at once to a dry acetone solution (150 ml.) of 3-(N-tert-butoxycarbonylamino)-3-phenyl-DL-propionic acid (10.8 g.) and triethylamine (4.1 g.) at $-10°$ to $-15°$ C with stirring. The resultant mixture was stirred at $-10°$ to $-15°$ C for an hour and thereto was added all at once a mixture of 7-amino-3-(5-methyl-1,3,4-thiadiazol-2-yl)thiomethyl-3-cephem-4-carboxylic acid (14.0 g.), triethylamine (12.2 g.), water (40 ml.) and acetone (160 ml.) at $-30°$ to $-40°$ C with stirring. The mixture was stirred at $-30°$ to $-40°$ C for 1.5 hours and furthermore at room temperature for 1.5 hours. After removing the acetone from the reaction mixture under reduced pressure, the resulting residue was washed with ethyl acetate. The water layer was separated, adjusted with 10% hydrochloric acid to about pH 1 and extracted with ethyl acetate (1000 ml.). The organic layer was washed with water and an aqueous solution of sodium chloride, dried over magnesium sulfate and treated with activated charcoal. The organic solution was then concentrated under reduced pressure to the volume of about 100 ml. and the concentrate was filtered to give 7-[3-(N-tert-butoxycarbonylamino)-3-phenyl-DL-propionamido]-3-(5-methyl-1,3,4-thiadiazol-2-yl)thiomethyl-3-cephem-4-carboxylic acid (1.48 g.), m.p. 150° to 155° C (dec.). The mother liquid was also concentrated under reduced pressure and depositted precipitate was filtered, in a condition of a little of ethyl acetate still remaining, to give the same object product (1.5 g.).

IR (Nujol): 3350, 1775, 1710, 1685, 1660, 1525 cm$^{-1}$
UV (Phosphate buffer, pH 6.4): $\lambda_{max} 272 m\mu$, E = 208.

The above mentioned 7-[3-(N-tert-butoxycarbonylamino)-3-phenyl-DL-propionamido]-3-(5-methyl-1,3,4-thiadiazol-2-yl)-thiomethyl-3-cephem-4-carboxylic acid (1.0 g.) was added to 50% formic acid and the mixture was stirred at 40° C for 3 hours. After the reaction mixture was concentrated to the volume of about 5 ml. under reduced pressure, water (ca. 2 ml.) and methyl isobutyl ketone containing Amberlite LA-1 (ca. 5 ml.) were added to the residue and then the mixture was stirred at room temperature overnight. The precipitate was filtered to give pale yellow powder of 7-(3-amino-3-phenyl-DL-propionamido)-3-(5-methyl-1,3,4-thiadiazol-2-yl)thiomethyl-3-cephem-4-carboxylic acid (170 mg.).

IR (Nujol): 3300, 1760, 1650, 1590, 1530 cm$^{-1}$.
UV (Phosphate buffer, pH 6.4): $\lambda_{max} 272$ m$\mu$, E = 205

EXAMPLE 2

3-(N-tert-butoxycarbonylamino)-3-(2-thienyl)-DL-propionic acid (10.8 g.) and triethylamine (4.04 g.) were dissolved in dry acetone (200 ml.) with stirring at room temperature. On cooling the solution at $-10°$ to $-15°$ C, pivaloyl chloride (4.82 g.) was added to the solution all at once with stirring. The mixture was stirred at $-10°$ to $-15°$ C for an hour and then cooled to $-40°$ to $-50°$ C. To the mixture was added a mixture of 7-amino-3-(5-methyl-1,3,4-thiadiazol-2-yl)thiomethyl-3-cephem-4-carboxylic acid (13.76 g.), triethylamine (12.0 g.), water (40 ml.) and acetone (160 ml.) all at once. The resultant mixture was stirred at $-40°$ to $-50°$ C for 1.5 hours and then at room temperature for 2 hours. The acetone was removed from the reaction mixture under reduced pressure and the residue was washed with ethyl acetate. The aqueous layer was separated, adjusted with 10% hydrochloric acid to pH 1 and extracted with ethyl acetate. The extract was washed with water and an aqueous solution of sodium chloride, dried over magnesium sulfate, treated with activated charcoal and then concentrated under reduced pressure. Ether was added to the concentrate and the mixture was stirred for 3 hours. The precipitate was filtered to give 7-[3-(N-tert-butoxycarbonylamino)-3-(2-thienyl)-DL-propionamido[-3-(5-methyl-1,3,4-thiadiazol-2-yl)thiomethyl-3-cephem-4-carboxylic acid (15.1 g.), m.p. 130° to 135° C (dec.).

IR (Nujol): 3350, 1780, 1710, 1690, 1650 cm$^{-1}$.
UV (Phosphate buffer, pH 6.4):
$\lambda_{max}$ 235 m$\mu$, E = 255;
$\lambda_{sh}$ 272 m$\mu$, E = 199.

The above obtained 7-[3-(N-tert-butoxycarbonylamino)-3-(2-thienyl)-DL-propionamido]-3-(5-methyl-1,3,4-thiadiazol-2-yl)thiomethyl-3-cephem-4-carboxylic acid (10 g.) in 99% formic acid (100 ml.) was stirred with ice-cooling for 2 hours. The reaction mixture was concentrated at a low temperature under reduced pressure to give a pale brown pasty residue. The concentrate was washed with ether (100 ml.), ethyl acetate (100 ml.) and acetonitrile (100 ml.) in turn. The precipitate was filtered to give pale yellow powder (5.6 g.). The above obtained product (4.3 g.) was dissolved in water (ca. 10 ml) and then Amberlite LA-1 (ca. 60 ml.) was added thereto. The mixture was stirred at room temperature overnight. The precipitate was filtered, triturated with acetone and washed with acetone and ether to give pale yellow powder (1.33 g.) of 7-[3-amino-3-(2-thienyl)-DL-propionamido]-3-(5-methyl-1,3,4-thiodiazol-2-yl)thiomethyl-3-cephem-4-carboxylic acid, m.p. 185° to 186° C (dec.). After the above obtained mother liquid was also concentrated under reduced pressure, the concentrate was washed with acetone and ether to give the same object product (1.1 g.). Total yield is 2.43 g.

IR (Nujol): 3300, 1780, 1660, 1630, 1580, 1520 cm$^{-1}$.
UV (Phosphate buffer, pH 6.4):
$\lambda_{max}$ 232 m$\mu$, E = 286;
$\lambda_{sh}$ 273 m$\mu$, E = 237.

EXAMPLE 3

3-(N-tert-butoxycarbonylamino)-3-phenyl-DL-propionic acid (5.26 g.) and triethylamine (2.02 g.) were added to acetone (150 ml.) and stirred at 5° C. An acetone solution (10 ml.) of pivaloyl chloride (2.41 g.) was added thereto at 5° C with stirring, and the resulting mixture was stirred for 30 minutes and cooled at −30° C. A solution of 7-amino-3-methylthio-3-chphem-4-carboxylic acid (5.7 g.) and triethylamine (4 g.) in dichloromethane (150 ml.) was added to the mixture all at once. The resultant mixture was stirred at −30° C for an hour, at 0° to 5° C for an hour and then at room temperature for 3 hours. After removal of the solvent under reduced pressure, the residue was dissolved in 5% aqueous solution of sodium hydrogen carbonate (100 ml.) and washed with ethyl acetate (200 ml.). The aqueous layer was separated, adjusted with concentrated hydrochloric acid to pH 2.0 and extracted with ethyl acetate (400 ml.). The extracted solution was washed with a saturated aqueous solution of sodium chloride (50 ml.), dried over magunesium sulfate and concentrated under reduced pressure. The concentrate was triturated with ether to give powder of 7-[3-(N-tert-butoxycarbonylamino)-3-phenyl-DL-propionamido]-3-methylthiomethyl-3-cephem-4-carboxylic acid (5.8 g.), m.p. 122° to 126° C (dec.).

UV (Phosphate buffer, pH 6.4): $\lambda_{max}$ 265 m$\mu$, E = 186.

The above obtained 7-[3-(N-tert-butoxycarbonylamino)-3-phenyl-DL-propionamido]-3-methylthiomethyl-3-cephem-4-carboxylic acid (3.0 g.) was added to formic acid (20 ml.). After stirring the mixture at room temperature for 3 hours, the solvent was removed under reduced pressure. Ethyl acetate was added to the residue and then the mixture was stirred. The resulting precipitate was collected by filtration and dried to give powder (2.6 g.). To the powder was added acetonitrile (20 ml.) and the mixture was stirred at room temperature for 5 hours, filtered and dried to give 7-(3-amino-3-phenyl-DL-propionamido)-3-methylthiomethyl-3-cephem-4-carboxylic acid (2.3 g.), m.p. 180° to 185° C (dec.).

UV (Phosphate buffer, pH 6.4): $\lambda_{max}$ 265 m$\mu$, E = 222.

EXAMPLE 4

3-(N-tert-butoxycarbonylamino)-3-phenyl-DL-propionic acid (7.89 g.) and 7-amino-3-(3-methyl-1,2,4-thiadiazol-5-yl)thiomethyl-3-cephem-4-carboxylic acid (11.35g.), as starting materials, were treated in a similar manner to that of Example 3 to give 7-[3-(N-tert-butoxycarbonylamino)-3-phenyl-DL-propionamido]-3-(3-methyl-1,2,4-thiadiazol-5-yl)thiomethyl-3-cephem-4-carboxylic acid (8.1 g.), m.p. 187° to 188° C (dec.).

UV (Phosphate buffer, pH 6.4): $\lambda_{max}$ 274 m$\mu$, E = 258.

The above obtained 7-[3-(N-tert-butoxycarbonylamino)-3-phenyl-DL-propionamido]-3-(3-methyl-1,2,4-thiadiazol-5-yl)thiomethyl-3-cephem-4-carboxylic acid (2.0 g.) was reacted with formic acid in a similar manner to that of the second half of Example 3 to give 7-(3-amino-3-phenyl-DL-propionamido)-3-(3-methyl-1,2,4-thiadiazol-5-yl)thiomethyl-3-cephem-4-carboxylic acid (1.8 g.), m.p. 135° to 140° C (dec.).

UV (Phosphate buffer, pH 6.4): $\lambda_{max}$ 274 m$\mu$, E = 274.

EXAMPLE 5

A mixture of 1-aminocyclohexane-1-acetic acid hydrochloride (3.87 g.) and thionyl chloride (2.3 ml.) in dichloromethane (50 ml.) was heated under reflux for 3 hours and then filtered. The filtrate was concentrated under reduced pressure and the residual pale yellow crystals were washed with dry ether and dissolved in dry dichloromethane (30 ml.). This solution was added dropwise to a mixed solution of 7-amino-3-methyl-3-cephem-4-carboxylic acid (4.28 g.), a dichloromethane solution (20 ml.) containing N-(trimethylsilyl)acetamide (433 mg./ml.) and dichloromethane (80 ml.) at −50° to −60° C with stirring over 15 minutes. The resultant mixture was stirred at −50° to −60° C for 2 hours and furthermore at room temperature for 2 hours. To the reaction mixture was added water and an insoluble substance was filtered off. The filtrate was washed with dichloromethane and then the aqueous layer was separated, adjusted to about pH 3.5 with sodium hydrogen carbonate, treated with activated charcoal and then concentrated under reduced pressure. The precipitate in the concentrate was filtered and then the filtrate was passed through an ion-exchange resin (IR-45, IRC-50). The precipitate was filtered to give 7-[2-(1-aminocyclohexan-1-yl) acetamido]-3-methyl-3-cephem-4-carboxylic acid (2.2 g.), m.p. 210° to 211° C (dec.). The mother liquid was concentrated under reduced pressure and then the precipitate in the concentrate was filtered off. The filtrate gave the same object product (1.3 g.) by scratching the inner wall of the reaction vessel. Total yield is 3.5 g.

UV (Phosphate buffer, pH 6.4): $\lambda_{max}$ 262 mµ, E = 212.

EXAMPLE 6

7-amino-3-methyl-3-cephem-4-carboxylic acid (4.28 g.) and N,N-bis(trimethylsilyl)acetamide (6.1 g.) were dissolved in dichloromethane (80 ml.). The dichloromethane solution (50 ml.) containing hydrochloric acid salt (4.4 g.) of 3-amino-3-phenyl-DL-propionyl chloride was added dropwise to the solution at −40° to −50° C with stirring over 10 minutes. The resultant mixture was stirred at −40° to −50° C for 1.5 hours and furthermore at room temperature for 1.5 hours and water (ca. 50ml.) was added and the aqueous mixture was stirred for 10 minutes. The aqueous layer was separated, treated with activated charcoal, adjusted with an aqueous solution of sodium hydrogencarbonate to pH 5 to 6 and left to stand at room temperature. The precipitate was filtered to give pale brown crystals of 7-(3-amino-3-phenyl-DL-propionamido)-3-methyl-3-cephem-4-carboxylic acid (1.8 g.), m.p. 244° to 245° C (dec.).

IR (Nujol): 3300, 1760, 1695, 1640, 1565, 1525, 700 cm$^{-1}$.

EXAMPLE 7

A mixture of 7-amino-3-methyl-3-cephem-4-carboxylic acid (4.28 g.) and N,N-bis(trimethylsilyl) acetamide (6.1 g.) in dichloromethane (80 ml.) was stirred at room temperature for 3 hours. To this mixture was added bit by bit hydrochloric acid salt (5.6 g.) of 3-amino-3-(2-thienyl)-DL-propionyl chloride. The resultant mixture was washed with dichloromethane (20 ml.) and stirred at −40° to −50° C for 1.5 hours and furthermore at room temperature for 1.5 hours. Water (ca. 50 ml.) was added thereto and the reaction mixture was stirred for 10 minutes. The aqueous layer was separated, treated with activated charcoal and adjusted with an aqueous solution of sodium hydrogen carbonate to pH 5 to 6. The precipitate was filtered and washed successively with acetone and ether to give whitish crystal (3.0 g.) of 7-[3-amino-3-(2-thienyl)-DL-propionamido]-3-methyl-3-cephem-4-carboxylic acid, m.p. 210° to 213° C (dec.). The mother liquid was concentrated to the volume of about 10 ml. under reduced pressure and left to stand at room temperature to give the same object product (0.8 g.). Total yield is 3.8 g.

IR (Nujol): 3350, 1770, 1730, 1695, 1560, 1530 cm$^{-1}$.

EXAMPLE 8

A mixture of 7-amino-3-methyl-3-cephem-4-carboxylic acid (2.14 g.) and N,N-bis(trimethylsilyl)acetamide (3.1 g.) in dichloromethane (80 ml.) was stirred at room temperature for 2 hours. After a solution of hydrochloric acid salt (2.6 g.) of 3-amino-3-cyclohexyl-DL-propionyl chloride in dry dichloromethane (50 ml.) was added to the mixture at −30° to −50° C all at once, the resultant mixture was stirred at the same temperature for 1.5 hours and furthermore at room temperature for 1.5 hours. Water was added to the reaction mixture, and the aqueous layer was separated, treated with activated charcoal and adjusted with an aqueous solution of sodium hydrogen carbonate to pH 5. The precipitate was filtered and washed successively with acetone and ether to give pale yellow crystals (1.1 g.) of 7-(3-amino-3-cyclohexyl-DL-propionamido)-3-methyl-3-cephem-4-carboxylic acid, m.p. 240° to 241° C (dec.)

IR (Nujol): 3300, 1770, 1690, 1640, 1570 cm$^{-1}$.

UV (Phosphate buffer, pH 6.4): $\lambda_{max}$ 262 mµ, E = 194.

EXAMPLE 9

A mixture of hydrochloric acid salt (3.87 g.) of 1-aminocyclohexane-1-acetic acid and phosphorus pentachloride (5.0 g.) in dry dichloromethane (100 ml.) was stirred at room temperature for 3 hours. An insoluble substance was removed by filtration and the filtrate was concentrated at a low temperature under reduced pressure. The concentrate was washed with dry ether and then dissolved in dichloromethane (50 ml.). The resultant solution was all at once added with stirring at −30° to −40° C to a solution prepared by dissolving a mixture of 7-amino-3-(5-methyl-1,3,4-thiadiazol-2-yl)-thiomethyl-3-cephem-4-carboxylic acid (6.88 g.) and N,N-bis(trimethylsilyl) acetamide (6.2 g.) in dichloromethane (150 ml.) at room temperature for an hour. The resultant mixture was stirred at −30° to −40° C for 1.5 hours and furthermore at room temperature for 1.5 hours. Water (ca. 50 ml.) was added to the reaction mixture, and the resulting insoluble substance was filtered off. The filtrate was adjusted with triethylamine to about pH 5 and concentrated at a low temperature under reduced pressure. Chloroform was added to the residue, and the mixture was stirred overnight, and centrifuged. The resultant solid was dissolved in 99% ethanol (200 ml.) and centrifuged again to give a solid, which was washed with acetone and ether to give brownish powder (4.5 g.) of 7-[2-(1-aminocyclohexan-1-yl)acetamido]-3-(5-methyl-1,3,4-thiadiazol-2-yl)thiomethyl-3-cephem-4-carboxylic acid, m.p. 176° to 178° C (dec.).

IR (Nujol): 3200, 1770, 1660, 1610 cm$^{-1}$.

UV (Phosphate buffer, pH 6.4): $\lambda_{max}$ 269 mµ, E = 187.

EXAMPLE 10

To a mixture of 7-[3-(N-tert-butoxycarbonylamino)-3-phenyl-DL-propionamido]cephalosproranic acid (2 g.) and 5-methyl-1,3,4-thiadiazole-2-thiol (0.5 g.) in phosphate buffer (pH 6.4, 60 ml.) was added sodium hydrogen carbonate (0.5 g.) little by little. The resultant solution was stirred at 60° C for 6 hours, cooled and shaked with ether. The aqueous layer was separated, adjusted with 10% aqueous hydrochloric acid to pH 2 under cooling and extracted with ethyl acetate. The organic layer was washed successively with water and a saturated aqueous solution of sodium chloride, dried over magnesium sulfate and concentrated under reduced pressure. The resulting residue was triturated with ether to give powder (0.85 g.) of 7-[3-(N-tert-butoxycarbonylamino)-3-phenyl-DL-propionamido]-3-(5-methyl-1,3,4-thiadiazol-2-yl)thiomethyl-3-cephem-4-carboxylic acid. This powder was dissolved in ethyl acetate and then most of ethyl acetate was removed under reduced pressure. After cooling, the precipitate was filtered and dried to give the object compound (0.55 g.), m.p. 148° to 154° C.

IR (Nujol): 3350, 1775, 1710, 1685, 1660, 1525 cm$^{-1}$.
UV (Phosphate buffer pH 6.4): $\lambda_{max}$ 272 mµ, E = 208.

EXAMPLE 11

3-[N-tert-butoxycarbonylamino]-3-phenyl-DL-propionyl chloride and 7-amino-3-[1-methyl-1H-tertrazol- 5-yl]thiomethyl-3-cephem-4-carboxylic acid, as starting materials, were treated in a similar manner to those of Examples given above to give 7-[3-amino-3-phenyl-DL-propionamido]-3-[1-methyl-1H-tetrazol-5-yl]thiomethyl-3-cephem-4-carboxylic acid.

EXAMPLE 12

3-[N-tert-butoxycarbonylamino]-3-(2-thienyl)-DL-propionyl chloride and 7-amino-3-(1-methyl-1H-tetrazol-5-yl)thiomethyl-3-cephem-4-carboxylic acid, as starting materials, were treated in a similar manner to those of Examples given above to give 7-[3-amino-3-(2-thienyl)-DL-propionamido]-3-(1-methyl-1H-tetrazol-5-yl)thiomethyl-3-cephem-4-carboxylic acid.

EXAMPLE 13

A solution of N-tert-butoxycarbonyl-β-alanine (2.97g.) and triethylamine (1.82g.) in dichloromethane (30ml.) was added dropwise to a solution of ethyl chloroformate (1.95g.) in dichloromethane (30ml.) at −10° C with stirring and then the mixture was stirred at −10° C for 30 minutes. To the mixture was added a solution of 7-amino-3-methyl-3-cephem-4-carboxylic acid (3.21g.) dissolved in dichloromethane (60ml.) with N,N-bis(trimethylsilyl)acetamide (6.1g.). After stirring at −10° C for 6 hours, the reaction mixture was washed with 5% aqueous hydrochloric acid and water. An insoluble substance was removed by filtration and then the mother solution was washed with water, dried and concentrated under reduced pressure to give oil (4.42g.) of 7-N-tert-butoxycarbonyl-β-alaninamido-3-methyl-3-cephem-4-carboxylic acid.

IR (liquid film): 3255, 1780, 1730, 1700, 1680 cm$^{-1}$.

A solution of 7-N-tert-butoxycarbonyl-β-alaninamido-3-methyl-3-cephem-4-carboxylic acid (2.62g.) in formic acid (40ml.) was stirred at 10° to 15° C for 3 hours. The reaction mixture was concentrated under reduced pressure, and the residue was dissolved in water. The resulting aqueous solution was washed with a little of ethyl acetate and subjected to lyophilization to give powder, which was suspended in 5% aqueous methanol (15ml.), stirred at room temperature for an hour. The resulting product was collected by filtration and washed with a little of methanol to give pure powder (1.6g.) of 7-β-alaninamido-3-methyl-3-cephem-4-carboxylic acid.

IR (nujol): 3260, 3130, 1740, 1653, 1612 cm$^{-1}$.

NMR (in D$_2$O + NaHCO$_3$):

ppm:
2.08 (s, 3H)
2.50 (t, 2H, J=6.5Hz)
3.29 (t, 2H, J=6.5Hz)
3.60, 3.25(AB-q, 2H, J=17Hz)
5.07 (d, 1H, J=4.5Hz)
5.55 (d, 1H, J=4.5Hz)

Analysis: Calcd. C 44.94, H 5.48, N 14.23. Found C 45.06, H 5.23, N 13.93.

EXAMPLE 14

A solution of N-tert-butoxycarbonyl-β-alanine (2.97g.) and triethylamine (1.82g.) in dichloromethane (60ml.) was added dropwise to a solution of ethyl chloroformate (1.95g.) in dichloromethane (60ml.) at −10° C with stirring and then the mixture was stirred at −10° C for 30 minutes. To the mixture was dropwise added a solution of 7-amino-3-(5-methyl-1,3,4-thiadiazol-2-yl)thiomethyl-3-cephem-4-carboxylic acid (6.16g.) dissolved in dichloromethane (60ml.) with N,N-bis(trimethylsilyl)acetamide (6.1g.). The resultant mixture was stirred at −5° - 0° C for 3 hours and furthermore at 5° − 10° C for 3 hours. The reaction mixture was washed successively with 5% aqueous hydrochloric acid and water, dried and concentrated to give oil (6.7g.) of 7-N-tert-butoxycarbonyl-β-alaninamido-3-(5-methyl-1,3,4-thiadiazol-2-yl)thiomethyl-3-cephem-4-carboxylic acid. The product was purified by column chromatography on silica gel (eluent: chloroform + methanol) to give pure product (5.88g.).

IR (liquid film): 3250, 1780, 1730, 1710, 1680 cm$^{-1}$

A solution of 7-N-tert-butoxycarbonyl-β-alaninamido-3-(2-methyl-1,3,4-thiadiazol-5-yl) thiomethyl-3-cephem-4-carboxylic acid (1.92g.) in formic acid (20ml.) was stirred at 10° to 15° C for 3 hours. Removing formic acid at room temperature under reduced pressure, water was added to the residue. The aqueous layer was washed with a little of ethyl acetate and then lyophilized to give powder. After the powder was suspended in 5% aqueous methanol, the suspension was stirred at room temperature for 2 hours, filtered and washed with a little of acetone to give 7-β-alaninamido-3-(5-methyl-1,3,4-thiadiazol-2-yl)thiomethyl-3-cephem-4-carboxylic acid (1.1g.).

IR (nujol): 3400, 3250, 1768, 1650, 1615 cm$^{-1}$

NMR (D$_2$O + DCl):

ppm:
2.83 (s, 3H)
2.86 (t, 2H, J=6.5Hz)
3.58 (t, 2H, J=6.5Hz)
3.98, 3.70 (AB-q, 2H, J=10Hz)
4.63, 4.50 (AB-q, 2H, J=13Hz)
5.19 (d, 1H, J=5Hz)
5.71 (d, 1H, J=5Hz)

We claim:

1. Compounds of the formula

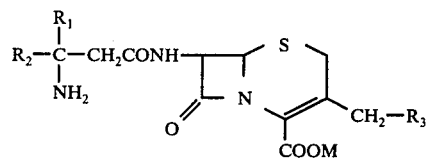

wherein
R$_1$ is hydrogen, lower alkyl having one to six carbon atoms, lower alkenyl having two to six carbon atoms, cyclohexyl, phenyl, or thienyl,
R$_2$ is hydrogen or lower alkyl having one to six carbon atoms, or
R$_1$ and R$_2$ taken together with the carbon to which they are attached is a cycloalkyl or cycloalkenyl group having from 5 to 7 carbon atoms,
R$_3$ is heterocyclicthio wherein the heterocyclic group is selected from the group consisting of 1,3,4-thiadiazolyl or 1,2,4-thiadiazolyl, and their lower alkyl derivatives, lower alkyl-1-H-tetrazolyl, and
M is hydrogen or a non-toxic, pharmaceutically acceptable cation.

2. A compound according to claim 1, wherein
R$_1$ is phenyl,
R$_2$ is hydrogen,
R$_3$ is 5-methyl-1,3,4-thiadiazol-2-ylthio, and
M is hydrogen.

3. A compound according to claim 1, wherein
R$_1$ is 2-thienyl,
R$_2$ is hydrogen,
R$_3$ is 5-methyl-1,3,4-thiadiazol-2-ylthio, and M is hydrogen.
4. A compound according to claim 1, wherein
$R_1$ is phenyl,
$R_2$ is hydrogen,
$R_3$ is 3-methyl-1,2,4-thiadiazol-5-ylthio, and
M is hydrogen.
5. A compound according to claim 1, wherein
$R_1$ is phenyl,
$R_2$ is hydrogen,
$R_3$ is 1-methyl-1H-tetrazol-5-ylthio, and
M is hydrogen.
6. A compound according to claim 1, wherein
$R_1$ is 2-thienyl,
$R_2$ is hydrogen,
$R_3$ is 1-methyl-1H-tetrazol-5-ylthio, and
M is hydrogen.
7. A compound according to claim 1, wherein
$R_1$ is hydrogen,
$R_2$ is hydrogen,
$R_3$ is 5-methyl-1,3,4-thiadiazol-2-ylthio, and
M is hydrogen.
8. A compound according to claim 1, wherein
$R_1$ and $R_2$ taken together with the carbon atom to which they are attached is cyclohexyl,
$R_3$ is 5-methyl-1,3,4-thiadiazol-2-ylthio,
M is hydrogen.

* * * * *